(12) United States Patent
Cipolletti et al.

(10) Patent No.: US 12,180,553 B2
(45) Date of Patent: Dec. 31, 2024

(54) TAGATOSE AND GALACTOSE SYRUP

(71) Applicant: INALCO S.R.L., Milan (IT)

(72) Inventors: Giovanni Cipolletti, Milan (IT); Luana Vagnoli, Quarata-Arezzo (IT); Jacopo Chini, Florence (IT); Silvia Biagiolini, Arezzo (IT)

(73) Assignee: INALCO S.R.L., Milan (IT)

( * ) Notice: Subject to any disclaimer, the term of this patent is extended or adjusted under 35 U.S.C. 154(b) by 826 days.

(21) Appl. No.: 17/284,716

(22) PCT Filed: Oct. 10, 2019

(86) PCT No.: PCT/EP2019/077459
§ 371 (c)(1),
(2) Date: Apr. 12, 2021

(87) PCT Pub. No.: WO2020/074635
PCT Pub. Date: Apr. 16, 2020

(65) Prior Publication Data
US 2021/0381068 A1 Dec. 9, 2021

(30) Foreign Application Priority Data
Oct. 12, 2018 (IT) .................. 102018000009407

(51) Int. Cl.
| | |
|---|---|
| *A23L 2/60* | (2006.01) |
| *A23C 9/13* | (2006.01) |
| *A23G 3/42* | (2006.01) |
| *A23L 27/30* | (2016.01) |
| *A23L 29/30* | (2016.01) |
| *A23L 33/125* | (2016.01) |
| *B01D 61/02* | (2006.01) |
| *B01D 61/14* | (2006.01) |
| *B01D 61/58* | (2006.01) |
| *C07H 1/06* | (2006.01) |
| *C07H 3/02* | (2006.01) |
| *C12P 19/02* | (2006.01) |
| *C12P 19/14* | (2006.01) |
| *C13K 13/00* | (2006.01) |

(52) U.S. Cl.
CPC ............ *C13K 13/00* (2013.01); *A23C 9/1307* (2013.01); *A23G 3/42* (2013.01); *A23L 2/60* (2013.01); *A23L 27/34* (2016.08); *A23L 29/37* (2016.08); *A23L 33/125* (2016.08); *B01D 61/025* (2013.01); *B01D 61/027* (2013.01); *B01D 61/145* (2013.01); *B01D 61/58* (2013.01); *C07H 1/06* (2013.01); *C07H 3/02* (2013.01); *C12P 19/02* (2013.01); *C12P 19/14* (2013.01); *A23V 2002/00* (2013.01); *B01D 2311/2623* (2013.01); *B01D 2317/02* (2013.01)

(58) Field of Classification Search
CPC .......... A23L 2/60; A23L 33/125; A23L 29/37; A23L 27/33; A23L 27/34; A23V 2250/28; A23V 2250/60; A23V 2250/614; A23V 2250/612; A23V 2250/608; A23V 2250/6406; A23V 2250/64; A23V 2250/634; A23V 2250/606; C07H 1/06; C07H 1/08; C07H 1/00
See application file for complete search history.

(56) References Cited

U.S. PATENT DOCUMENTS

| | | | |
|---|---|---|---|
| 4,273,922 A | 6/1981 | Hicks | |
| 6,057,135 A | 5/2000 | Ibrahim et al. | |
| 2010/0234587 A1 | 9/2010 | Vagnoli et al. | |
| 2012/0189739 A1* | 7/2012 | Rathke | ............ A23L 27/36 426/597 |

FOREIGN PATENT DOCUMENTS

| | | | |
|---|---|---|---|
| EP | 2870243 A1 | 5/2015 | |
| WO | 2014006606 A1 | 1/2014 | |
| WO | WO-2016120228 A1 * | 8/2016 | ............ A23K 20/10 |

OTHER PUBLICATIONS

International Search Report and Written Opinion for PCT/EP2019/077459, dated Jan. 23, 2020.
Corriher, Shirley, "Learn How to Control Crystallization for Successful Sweets," Fine Cooking, Issue 36 (1999) (Retrieved from https://web.archive.org/web/20170530113818/http://www.finecooking.com/author/chirley-corriher on May 28, 2019).
First Office Action in Chinese Invention Patent Application No. 201980067240.4, dated Feb. 15, 2023.

* cited by examiner

*Primary Examiner* — Hong T Yoo
(74) *Attorney, Agent, or Firm* — Troutman Pepper Hamilton Sanders LLP

(57) ABSTRACT

The present invention describes a syrup of tagatose and galactose as main components together with other secondary products such as glycerol, oligosaccharides and other sugars in a minority amount.

16 Claims, 2 Drawing Sheets

TAGATOSE AND GALACTOSE SYRUP

This application is a national stage application under 35 U.S.C. § 371 of PCT Application No. PCT/EP2019/077459, filed Oct. 10, 2019, which claims the priority benefit of Italian Patent Application No. 102018000009407, filed Oct. 12, 2018, which are hereby incorporated by reference in their entirety.

FIELD OF THE INVENTION

The present invention relates to the field of sweeteners and prebiotics.

BACKGROUND

Tagatose is a hexose ketonic monosaccharide, isomer of fructose. It is a rare sugar that can be found in small amounts in dairy products if subjected to heating.

Despite having a sweetening power equal to 92% with respect to sucrose, it provides a reduced caloric intake (38%), it is not cariogenic and it therefore finds application as a sweetener instead of the common table sugar also in the preparation of bakery products in the confectionery industry.

Tagatose has an anti-hyperglycemic effect because it manages to control the level of postprandial blood glucose by increasing the activity of the enzyme glucokinase responsible for the transfer of glucose in the glycogen. It also has an inhibiting effect on some enzymes involved in the degradation of carbohydrates in the bowel causing a decrease in their absorption.

Studies have been conducted on the effect of reduction of the glycemic index caused by the intake of tagatose (Mark Ensor, et al. "*Effect of Three Low-Doses of D-Tagatose on Glycemic control Over Six Months in Subjects with Mild Type 2 Diabetes Mellitus with Diet and Exercise*" J Endocrinol Diabetes Obes. 2014 October; 2 (4): 1057).

Therefore, tagatose is useful in the treatment of type 2 diabetes mellitus for which clinical studies have been performed (ClinicanTrials.gov, NCT00955747, first posted: Aug. 10, 2009).

However, the use of tagatose in crystalline form as a sweetener and as a prebiotic in food products, sports drinks, etc. is inhibited by the cost of the product which is often not very competitive with respect to other synthetic or extractive molecules.

Galactose is a simple sugar, epimer of glucose. It is produced in small amounts in the human body while most of it is introduced with the diet mainly through the intake of milk and dairy products that contain the lactose disaccharide which through the enzyme lactase is broken down into glucose and galactose.

Lactose is the sugar that is most present in the infant's feeding who, being a growing organism, needs to have an efficient source of energy available and furthermore there is experimental evidence that the galactose derived therefrom is involved in the process of myelin formation (Ravera S, Bartolucci M, Cazia D, Morelli A, Panfoli I, "*Galactose and Hexose 6-Posphate Dehydrogenase Support the Myelin Metabolic Role*", PARIPEX Indian journal of research 2015, 4 (9) PP 21-24).

Various studies have been conducted on the positive effects of galactose on the central nervous system, for the treatment of degenerative diseases such as for example Alzheimer disease ("*Therapeutic effect of oral galactose treatment in rat model of sporadic Alzheimer's*" Alzheimer's & Dementia—The Journal of the Alzheimer's Association disease, July 2014, volume 10, issue 4, supplement page P464).

There is experimental evidence that the intake of galactose and antioxidants may also be useful in the treatment of multiple sclerosis especially in the early stages of the onset of the disease (Isabella Pandolfi, et al, "*Missed evolution of demyelinating brain during supplementation with natural compounds: A case report*", Medical Research Archives, vol. 4, issue 1, April 2016.

Clinical studies are underway for the use of galactose as a food supplement in the treatment of congenital glycosylation disorder (ClinicanTrials.gov, NCT02955264, first posted: Nov. 4, 2016) and in the treatment of type 2 diabetes (ClinicanTrials.gov, NCT01776099, first posted: Jan. 25, 2013).

Are now known the many beneficial properties on the health of oligosaccharides such as galacto-oligosaccharides which are formed thanks to the action of the enzyme lactase (beta-galactosidase) which, in addition to having a hydrolytic activity on lactose, also has a synthetic action adding galactose units to the latter in a variable number.

The galacto-oligosaccharides have a probiotic effect promoting the growth of microorganisms in the bowel (mainly bifidobacteria) and, according to several studies they might inhibit the growth of potentially pathogenic microorganisms (Daniele Garrido, et al., "*Utilization of galactooligosaccharides by Bifidobacterium longum subsp. Infantis isolates*", Food Microbiol. 2013 April 33 (2); 262-270).

The object of the present invention is to provide a syrup based on tagatose and galactose and preparation method thereof.

SUMMARY OF THE INVENTION

The present invention solves the aforementioned problems by means of a composition comprising:

| | |
|---|---|
| tagatose | 40-50% |
| galactose | 30-40% |
| oligosaccharides(GLT) | 7-10% |
| glycerol | 4-10% |
| other sugars | 2-8% |
| lactose | ≤1% |
| lactulose | ≤1% | wherein the tagatose/galactose ratio is equal to 1.0-1.6, in which the % are by weight on the dry composition, said composition in syrup form at a saccharometric concentration of 58-62° brix.

The object of the present invention is therefore a syrup of tagatose and galactose as main components together with other secondary products such as glycerol, oligosaccharides and other sugars in a minority amount. The composition of the present invention makes it possible to avoid the passage of crystallization of the tagatose (which inevitably leads to the loss of product in the crystallization mother liquors) as well as allowing a shortening of the production times with an increase in productivity, for the benefit of the final cost.

Therefore the advantage of the composition in the form of syrup is evident, however, it should be emphasized that one of the problems of sugary syrups is that depending on the degree of purity and storage conditions they tend to crystallize, but in the case of the present composition it has surprisingly been found that the ratio equal to 1.0-1.6 between tagatose and galactose prevents this from occurring with undoubted advantages from a commercial point of view and of use of the product.

Nevertheless the composition of the present invention, besides providing an intake of tagatose, also allows other substances to be introduced into the diet such as galactose and galacto-oligosaccharides which, for the reasons mentioned, can act synergistically, also providing a positive contribution to health. The syrup of the present invention, due to the beneficial effects of tagatose and galactose, can be used in the preparation of functional foods, medical foods, sports drinks, fruit juices, yoghurts, food supplements and in the confectionery industry.

The object of the present invention is also a process for the preparation of the aforementioned syrup, said process comprising:
  i. subjecting lactose to enzymatic hydrolysis by a lactase enzyme to obtain a mixture comprising glucose and galactose;
  ii. putting the mixture comprising glucose and galactose in contact with at least one food yeast to perform deglucosation and obtain a deglucosed mixture;
  iii. subjecting the deglucosed mixture to alkaline epimerization to perform epimerization of the galactose to tagatose and obtain an epimerized mixture;
  iv. putting the epimerized mixture in contact with at least one ion-exchange resin to perform deionization and obtain a deionized mixture;
  V. optionally subjecting the deionized mixture to nano-filtration to obtain a nanofiltered mixture;
  vi. optionally subjecting the deionized mixture, or optionally the nanofiltered mixture, to reverse osmosis to obtain an osmotic retentate;
  vii. subjecting the deionized mixture, or optionally the nanofiltered mixture, or optionally the osmotic retentate to ceramic ultrafiltration to obtain an ultrafiltrated mixture;
  viii. subjecting the ultrafiltrated mixture to a concentration of up to 58-62° brix to obtain the syrup.

DETAILED DESCRIPTION OF THE INVENTION

Figure 1:
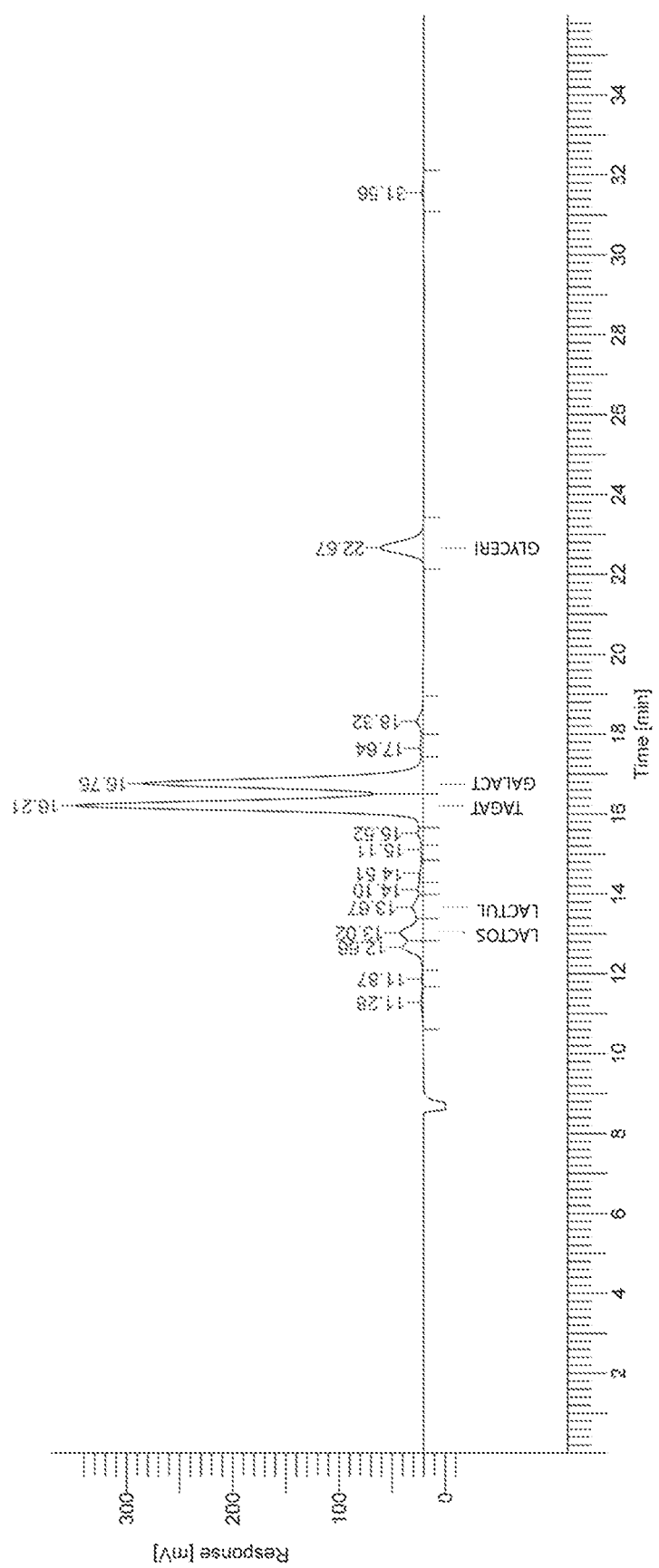
FIG. 1—Example of an HPLC chromatogram on a sulphonic column of a composition according to the invention.

The syrup of the present invention preferably has a tagatose/galactose ratio equal to 1.1-1.5, more preferably 1.2-1.4.

The syrup of the present invention preferably has a saccharometric concentration of 59-61° brix.

The syrup of the present invention preferably has a pH of 3.0-3.5.

Preferably, the composition of the present invention comprises:

| | |
|---|---|
| tagatose | 43-47% |
| galactose | 30-36% |
| oligosaccharides(GLT) | 7-10% |
| glycerol | 8-10% |

-continued

| | |
|---|---|
| other sugars | 2-5% |
| lactose | ≤1% |
| lactulose | ≤1% |

According to the process of the present invention the raw material is preferably lactose monohydrate in crystalline form. Alternatively, other sources of lactose can also be used, such as for example whey.

The enzymatic hydrolysis (i) of lactose is carried out using the commercial lactase enzyme of various origin; for example and preferably: from *K. Lactis, K. Fragilis, A oryzae, A. niger, E. coli, B. stearothermophilus, B. circulans* more preferably in the present invention the enzyme from *A. oryzae* is used.

The lactase enzyme can be used both in free and immobilized form on solid supports of various kinds, for example and preferably immobilized on synthetic resins, alginate beads, synthetic membranes or cotton fibre, preferably the immobilized enzyme is used in the present invention on a polystyrene synthetic resin, more preferably an immobilized enzyme as described in the patent application WO2014006606.

The enzymatic hydrolysis (i) reaction of the lactose is carried out at a temperature comprised between 5 and 60° C., preferably at 52° C. and at a pH of 4.0-9.0, preferably 5.1-5.5, keeping the lactose solution under recirculation on the column for a time comprised between 1 and 48 hours, preferably 20 hours.

According to the present invention, the solution containing the lactose hydrolyzed to glucose and galactose is subjected to a deglucosation step (ii) by adding a food yeast, preferably lyophilized beer yeast (*S. cerevisiae*), until a glucose concentration ≤0.25% is obtained. The deglucosation is preferably performed under insufflation of air by keeping under stirring at a temperature comprised between 25 and 40° C., preferably between 3° and 37° C., more preferably at 35° C., at a pH of 4.0-9.0, preferably 6.0-7.0, for a time of at least 4 hours.

The galactose present in the deglucosed solution is converted into tagatose by epimerization (iii) by the addition of an alkaline substance for example and preferably sodium hydroxide, potassium hydroxide or calcium hydroxide, more preferably according to the present invention calcium hydroxide is used. The alkaline substance is preferably used with a molar ratio of 0.1-1.0, preferably 0.4-0.8, more preferably 0.6, moles of alkaline substance per mole of galactose. The epimerization (iii) is preferably conducted keeping under stirring at a temperature of 0-30° C., preferably 5-25° C., more preferably 10-20° C., for a time of at least 10 minutes, preferably 4 hours.

At the end the epimerization reaction (iii) is neutralized by adding an acid preferably selected among the group consisting of hydrochloric acid, phosphoric acid, sulfuric acid, more preferably 30-50% sulfuric acid is used in water. After neutralization with the acid the suspension is preferably centrifuged to separate the precipitated calcium sulfate and the residual yeasts from the deglucosation step.

The solution obtained after neutralization and centrifugation is deionized (iv) through the passage on a pair of ion-exchange resins, preferably a strong cationic resin (such as for example Rohm and Haas Amberlite™.200 C, Rohm and Haas Amberlite™.IR120, Rohm and Haas Amberlite™.FPC 23 and Dowex™ Monosphere™ 88,) followed by a weak anionic resin (such as for example: Dow®

Amberlite™ FPA 55, Dowex™ Monosphere™ 66, Rohm and Haas Amberlite™.IRA 96, Purolite® A 120S and Purolite® A 109).

The deionized mixture can be, optionally but preferably, in order to at least partially remove oligomeric components from dimers upwards, then subjected to nanofiltration (v). Said nanofiltration is preferably on a spiral wound membrane selected for example among the group consisting of Dow Filmtec™ NF270-4040, Koch Membrane System TFC-SR2 or analogues recovering the permeate which is then subjected, optionally and preferably in order to at least partially remove the glycerol, to a reverse osmosis treatment (vi) on a reverse osmosis membrane for example and preferably selected among the group consisting of Es. Dow Filmtec™ BW30-4040.

According to the present invention, the retentate obtained in the reverse osmosis step (vi) is clarified by ultrafiltration (vii) on a ceramic membrane, preferably 300000 Da cut-off, recovering the permeate which is subjected to concentration (viii). After correcting the pH, preferably by adding an organic acid, at a value comprised between 3.0 and 3.5, the syrup is concentrated up to obtaining a syrup with a saccharometric concentration of 60±2° Bx. Said organic acid is preferably selected among the group consisting of citric acid, lactic acid, acetic acid. Preferably the organic acid used to correct the pH is citric acid, more preferably an aqueous solution of citric acid at 40-60% by weight.

The present invention can be better understood in light of the following embodiment examples.

EXPERIMENTAL PART

HPLC Method:

Perkin Elmer 200 series chromatograph with refractive index detector with thermostated cells.

Analysis on sulphonic column: Transgenomic ICE-SEP ION 300 column with pre-column. Temperature 45° C., Flow 0.4 ml/min, eluent Sulfuric acid 0.015N.

Analysis on amine column: Thermo Scientific™ Hypersil™ APS-2. Temperature 40° C., Flow 1.1 ml/min, Mobile phase=Acetonitrile+sodium phosphate monobasic dihydrate 1.45 g/litre.

Example 1: Enzymatic hydrolysis of Lactose on an industrial scale and obtainment of the deglucosed solution.

a) Preparation of the Immobilized Enzyme on Synthetic Resin:

In a 10 m3 steel jacketed reactor provided with thermostatation, 750 litres of Purolite A 120 S resin were loaded. The resin was washed with three 750-litre aliquots of drinking water each. 480 litres of a 100 mM sodium acetate solution at pH 5 and 55 Kg of a 50% glutaraldehyde solution were added. The whole was kept under stirring at 25° C. for 30 hours after which the resin was washed with three 1000-litre aliquots of drinking water each. 2000 litres of a 100 mM sodium acetate solution at pH 5 and 30 kg of lactase enzyme from *A. oryzae* were added. The whole was kept under stirring at 25° C. for 65 hours. After this time had elapsed, the resin was washed with three 2000-litre aliquots of drinking water each.

b) Enzymatic Hydrolysis of Lactose:

2000 kg of lactose monohydrate in crystalline form were solubilized in 8000 litres of drinking water in a 10 m3 steel reactor provided with stirring and thermostatation jacket. The internal temperature of the reactor was brought to 53° C. and the pH to 5.39 by adding 38% Sulfuric acid.

The lactose solution was recirculated through a column containing 600 litres of resin (with the lactase enzyme immobilized as described above in example 1a) at a flow rate of 2400 litres/hour for 20 hours.

Analytical Results on Sulphonic Column:

| Galactose (HPLC) | 9.023% |
| Glucose (HPLC) | 9.228% |
| Lactose (HPLC) | 0.492% |
| Glucose/galactose | 1.02 |

After this time has elapsed, the solution containing glucose and galactose is transferred to a 20 m3 steel jacketed reactor provided with stirring and an air insufflation system. The temperature was brought to 35° C. and 12 kg of lyophilized beer yeast and 100 ml of defoamer (Silifood 1600) were added to the solution.

The whole was kept under stirring at 35±2° C. for 10 hours with insufflation of air.

After this time had elapsed, the pH was brought back to 6.8 by adding 9 litres of 30% sodium hydroxide. At the end of the pH correction, 10 kg of lyophilized beer yeast were introduced into the reactor and the fermentation was kept under stirring with insufflation of air for further 10 hours. After this time had elapsed, the pH was adjusted to 6.6 by adding 15 litres of 30% sodium hydroxide and 10 kg of lyophilized beer yeast were introduced. After the further 15 hours had elapsed, the deglucosed solution obtained was cooled to about 5° C.

Analytical Results on Sulphonic Column:

| Galactose (HPLC) | 8.058% |
| Glucose (HPLC) | 0.013% |
| Lactose (HPLC) | 0.491% |
| Glucose/galactose | 0.2 |

Example 2: Laboratory-scale epimerization with 50% moles of calcium hydroxide with respect to galactose moles at 40° C. starting from the deglucosed solution of example 1.

250 g of the deglucosed galactose solution prepared according to example 1 were introduced into a 1 litre glass reactor, thermostated and provided with a stirring rod and combined to 4.16 g of calcium hydroxide (ventilated lime) keeping the whole under stirring at a temperature of 40° C.

Samples were taken for HPLC analysis on sulphonic column after: 120 min., 240 min., 360 min.

The Results are Expressed in the Following Table:

| Time (minutes) | Gal/(Gal + Tag)*100 | Tag/(Gal + Tag)*100 |
|---|---|---|
| 120 | 36% | 64% |
| 240 | 38% | 62% |
| 360 | 40% | 60% |

Example 3: Laboratory-scale epimerization with 60% moles of calcium hydroxide with respect to galactose moles at 40° C. starting from the deglucosed solution of example 1.

250 g of the deglucosed galactose solution prepared according to example 1 were introduced into a 1 litre glass reactor, thermostated and provided with a stirring rod and combined to 5.0 g of calcium hydroxide (ventilated lime) keeping the whole under stirring at a temperature of 40° C.

Samples were taken for HPLC analysis on sulphonic column after: 120 min., 240 min., 360 min.

The Results are Expressed in the Following Table:

| Time (minutes) | Gal/(Gal + Tag)*100 | Tag/(Gal + Tag)*100 |
| --- | --- | --- |
| 120 | 32% | 68% |
| 240 | 34% | 66% |
| 360 | 40% | 60% |

Example 4: Laboratory-scale epimerization with 50% moles or calcium nydroxide with respect to galactose moles at 30° C. starting from the deglucosed solution of example 1.

250 g of the deglucosed galactose solution prepared according to example 1 were introduced into a 1 litre glass reactor, thermostated and provided with a stirring rod and combined to 4.16 g of calcium hydroxide (ventilated lime) keeping the whole under stirring at a temperature of 30° C.

Samples were taken for HPLC analysis on sulphonic column after: 120 min., 280 min., 350 min.

The Results are Expressed in the Following Table:

| Time (minutes) | Gal/(Gal + Tag)*100 | Tag/(Gal + Tag)*100 |
| --- | --- | --- |
| 120 | 36% | 64% |
| 280 | 39% | 61% |
| 350 | 40% | 60% |

Example 5: Laboratory-scale epimerization with 60% moles of calcium hydroxide with respect to galactose moles at 30° C. starting from the deglucosed solution of example 1.

250 g of the deglucosed galactose solution prepared according to example 1 were introduced into a 1 litre glass reactor, thermostated and provided with a stirring rod and combined to 5.0 g of calcium hydroxide (ventilated lime) keeping the whole under stirring at a temperature of 30° C.

Samples were taken for HPLC analysis on sulphonic column after: 120 min., 280 min., 350 min.

The Results are Expressed in the Following Table:

| Time (minutes) | Gal/(Gal + Tag)*100 | Tag/(Gal + Tag)*100 |
| --- | --- | --- |
| 120 | 33% | 67% |
| 280 | 37% | 63% |
| 350 | 40% | 60% |

Example 6: Laboratory-scale epimerization with 50% moles of calcium hydroxide with respect to galactose moles at 25° C. starting from the deglucosed solution of example 1.

250 g of the deglucosed galactose solution prepared according to example 1 were introduced into a 1 litre glass reactor, thermostated and provided with a stirring rod and combined to 4.16 g of calcium hydroxide (ventilated lime) keeping the whole under stirring at a temperature of 25° C.

Samples were taken for HPLC analysis on sulphonic column after: 120 min, 280 min, 350 min, 470 min, 590 min, 710 min, 790 min.

The Results are Expressed in the Following Table:

| Time (minutes) | Gal/(Gal + Tag)*100 | Tag/(Gal + Tag)*100 |
| --- | --- | --- |
| 120 | 61% | 39% |
| 280 | 54% | 46% |
| 350 | 50% | 50% |
| 470 | 47% | 53% |
| 590 | 45% | 55% |
| 710 | 44% | 56% |
| 790 | 43% | 57% |

Example 7: Laboratory-scale epimerization with 60% moles of calcium hydroxide with respect to galactose moles at 25° C. starting from the deglucosed solution of example 1.

250 g of the deglucosed galactose solution prepared according to example 1 were introduced into a 1 litre glass reactor, thermostated and provided with a stirring rod and combined to 5.0 g of calcium hydroxide (ventilated lime) keeping the whole under stirring at a temperature of 25° C.

Samples were taken for HPLC analysis on sulphonic column after: 120 min., 280 min., 350 min., 470 min., 590 min., 710 min, 790 min.

The Results are Expressed in the Following Table;

| Time (minutes) | Gal/(Gal + Tag)*100 | Tag/(Gal + Tag)*100 |
| --- | --- | --- |
| 120 | 52% | 48% |
| 280 | 44% | 56% |
| 350 | 40% | 60% |
| 470 | 37% | 63% |
| 590 | 35% | 65% |
| 710 | 34% | 66% |
| 790 | 33% | 67% |

Example 8: Obtainment of the Tagatose/galactose syrup on an industrial scale starting from the deglucosed solution of example 1.

Alkaline Epimerization:

9100 kg of deglucosed galactose solution prepared according to example 1 were introduced into a 10 m3 steel reactor provided with stirring and thermostatation jacket. 192.4 Kg of calcium hydroxide were added in the 30% suspension of drinking water (the amount of calcium hydroxide represents a molar ratio of 60% with respect to galactose). After the addition the temperature was kept at 15±5° C. for 4 hours under stirring. After this time had elapsed, the pH of the suspension was brought to 2.5 by adding 590 litres of 38% sulfuric acid, keeping the temperature below 45° C. The temperature was then lowered to 25° C. and precipitated calcium sulfate was separated by 8 centrifugations at 350 rpm for 25 minutes.

Analytical Results on Sulphonic Column:

| | |
| --- | --- |
| Tagatose (HPLC) | 3.314% |
| Galactose (HPLC) | 2.746% |
| Gal/(Gal + Tag)*100 | 45% |
| Tag/(Gal + Tag)*100 | 55% |

Deionization on Ion-Exchange Resins:

The solution obtained in the previous centrifugation step was deionized on a pair of ion-exchange resins (4000 litres of strong cationic resin Amberlite™ FPC 23 and 4000 litres of weak anionic resin Amberlite™ FPA 55) at a flow rate of 2000 litres/hour collecting the eluted product from the resins up to a sugar concentration ≥0.5° Bx and a conductivity ≤50 µs/cm.

Nanofiltration:

The deionized solution was then subjected to a nanofiltration step using a system consisting of 12 membranes (DOW® FILMTECH™ NF 270 40/40) at a pressure of about 30 bar.

Reverse Osmosis:

The permeate of the nanofiltration was subjected to a reverse osmosis step using a system consisting of 12 membranes (DOW® FILMTECH™ BW30-400) at a pressure of about 10 bar concentrating the retentate up to a sugar concentration of 10° Bx.

Ceramic Ultrafiltration:

The concentrated solution was clarified by a tangential ultrafiltration step on a 300000 Da c.o. ceramic membrane at a permeation flow rate of 2000 litres/hour and retentate recirculation of 9000 litres/hour. The retentate was concentrated up to about 300 litres and washed 3 times with 150 litres of drinking water each.

Concentration:

The clarified permeate from the previous ultrafiltration step was transferred to a 5000 litre steel reactor provided with stirring, thermostatation jacket and a condenser.

The pH was brought to 3.0 by adding 1.6 litres of 50% citric acid in water and the solution was concentrated under vacuum at a temperature of about 50° C. up to a saccharometric concentration of 60° Bx.

Figure 2:
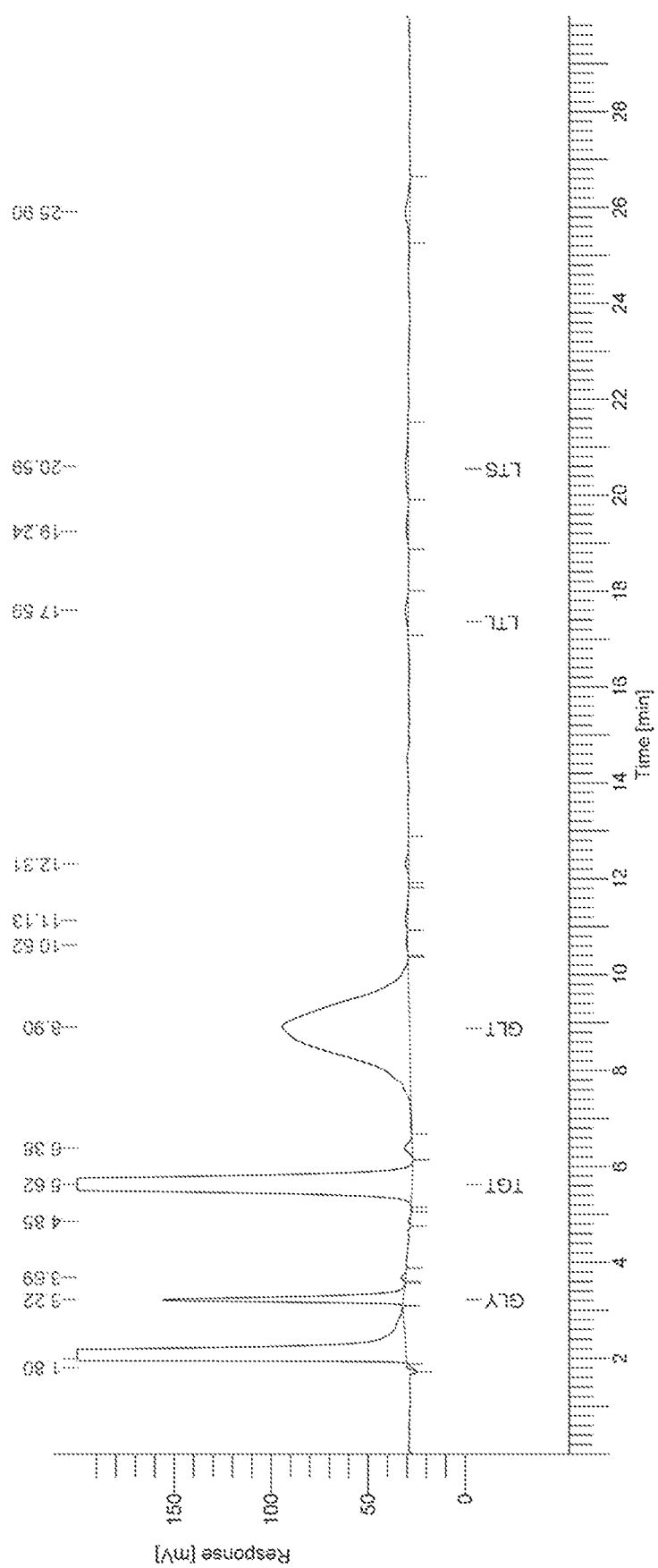
FIG. 2—Example of an HPLC chromatogram on an amine column of a composition according to the invention.

Results:

the syrup obtained at the end of the process was analyzed both on a sulphonic and amine column, the latter for the determination of the lactose content (see also HPLC traces in FIGS. 1 and 2) and the results are expressed in the following table:

| | |
|---|---|
| Refractometric dry substance | 60° Bx |
| Tagatose | 45.2% (on dry weight) |
| Galactose | 33.8% (on dry weight) |
| Tagatose/galactose ratio | 1.3 |
| Other Substances | |
| Lactose | 0.3% (on dry weight) |
| Lactulose | 0.4% (on dry weight) |
| Glycerol | 8.9% (on dry weight) |
| Oligosaccharides (GLT) | 8.0% (on dry weight) |
| Other sugars | 2.4% (on dry weight) |
| pH | 2.9 |
| Sulfuric ashes | 0.1% |
| Density | 1284 g/ml |
| T.A.M.C. | 5 ufc/g |
| T.Y.M.C. | 0 ufc/g |
| *Salmonella* sp. | Absent ufc/10 g |
| *Escherichia coli* | Absent ufc/g |
| Enterobacteriaceae | Absent ufc/g |

The invention claimed is:

1. A composition consisting of:

| | |
|---|---|
| tagatose | 40-50% |
| galactose | 30-40% |
| oligosaccharides | 7-10% |
| glycerol | 4-10% |
| other sugars | 2-8% |
| lactose | ≤1% |
| lactulose | ≤1% | wherein the tagatose/galactose ratio is in a range of 1.0 to 1.6, in which the % are by dry weight, said composition in syrup form at a saccharometric concentration of 58-62° brix.

2. The composition according to claim 1, wherein the tagatose/galactose ratio is in a range of 1.1 to 1.5.

3. The composition according to claim 1, having the saccharometric concentration of 59-61° brix.

4. The composition according to claim 1, having a pH in a range of 3.0 to 3.5.

5. The composition according to claim 1, consisting of:

| | |
|---|---|
| tagatose | 43-47% |
| galactose | 30-36% |
| oligosaccharides | 7-10% |
| glycerol | 8-10% |
| other sugars | 2-5% |
| lactose | ≤1% |
| lactulose | ≤1%. |

6. A process for the preparation of the syrup according to claim 1, said process comprising:
   i. subjecting lactose to enzymatic hydrolysis by a lactase enzyme to obtain a mixture comprising glucose and galactose;
   ii. putting the mixture comprising glucose and galactose in contact with at least one food yeast to perform deglucosation and obtain a deglucosed mixture;
   iii. subjecting the deglucosed mixture to alkaline epimerization to perform epimerization of the galactose to tagatose and obtain an epimerized mixture;
   iv. putting the epimerized mixture in contact with at least one ion-exchange resin to perform deionization and obtain a deionized mixture;
   v. subjecting the deionized mixture to ceramic ultrafiltration to obtain an ultrafiltrated mixture;
   vi. subjecting the ultrafiltrated mixture to a concentration of up to 58-62° brix to obtain the syrup according to claim 1.

7. The process according to claim 6, wherein the lactose is lactose monohydrate in crystalline form.

8. The process according to claim 6, wherein the lactose enzymatic hydrolysis (i) reaction is carried out at a temperature comprised between 5° C. and 60° C. and at a pH in a range of 4.0 to 9.0, keeping a lactose solution under recirculation on a column for a time comprised between 1 and 48 hours, where the column comprises an immobilized lactase enzyme from *K. Lactis, K. Fragilis, A. oryzae, A. niger, E. coli, B. stearothermophilus* or *B. circulans*.

9. The process according to claim 8, wherein the lactose solution is kept under the recirculation on the column for 20 hours.

10. The process according to claim 6, wherein the deglucosation is performed under insufflation of air, keeping under stirring at a temperature comprised between 25° C. and 40° C. and at a pH range of 4.0 to 9.0 for a time of at least 4 hours.

11. The process according to claim 6, wherein the epimerization (iii) occurs by the addition of calcium hydroxide at a molar ratio range of 0.1 to 1.0, with respect to the galactose moles; said epimerization (iii) conducted under stirring at a temperature range of 0° C. to 30° C., for a time of at least 10 minutes; wherein at its end the epimerization reaction (iii) is neutralized at the end of the reaction by adding 30 to 50% sulfuric acid in water; and wherein, after neutralization with the acid, the suspension is centrifuged to separate the precipitated calcium sulphate and the residual yeasts from the deglucosation step.

12. The process according to claim 11, wherein said epimerization is conducted under the stirring for 4 hours.

13. The process according to claim 6, further comprising subjecting the deionized mixture to nanofiltration to obtain a nanofiltered mixture, and then subjecting the nanofiltered mixture to ceramic ultrafiltration to obtain the ultrafiltrated mixture.

14. The process according to claim 13, further comprising subjecting the nanofiltered mixture to reverse osmosis to obtain an osmotic retentate, and then subjecting the osmotic retentate to ceramic ultrafiltration to obtain the ultrafiltrated mixture.

15. The process according to claim 6, further comprising subjecting the deionized mixture to reverse osmosis to obtain an osmotic retentate and then subjecting the osmotic retentate to ceramic ultrafiltration to obtain the ultrafiltrated mixture.

16. A method of preparing a functional food, a medical sport drink, a fruit juice, a yoghurt, a food supplement, or confectionery industry preparation, said method comprising: adding the composition according to claim 1.

* * * * *